United States Patent [19]

Grim

[11] Patent Number: 5,062,414

[45] Date of Patent: Nov. 5, 1991

[54] SIMPLIFIED ORTHOPAEDIC BACK SUPPORT

[75] Inventor: Tracy E. Grim, Broken Arrrow, Okla.

[73] Assignee: Royce Medical Company, Westlake Village, Calif.

[21] Appl. No.: 464,360

[22] Filed: Jan. 11, 1990

Related U.S. Application Data

[63] Continuation-in-part of Ser. No. 308,687, Feb. 8, 1989, Pat. No. 4,993,409.

[51] Int. Cl.⁵ ................................................ A61F 5/00
[52] U.S. Cl. .................................... 128/68.1; 128/362; 128/384; 128/400; 128/DIG. 20
[58] Field of Search ..................... 128/68.1, 78, 82.1, 128/85, 87 R, 118.1, 362, 379, 384, 400, DIG. 20

[56] References Cited

U.S. PATENT DOCUMENTS

| | | |
|---|---|---|
| 3,548,420 | 12/1970 | Spence . |
| 3,548,819 | 12/1970 | Davis et al. . |
| 3,578,773 | 5/1971 | Schultz ................................. 128/78 |
| 4,135,503 | 1/1979 | Romano ................................ 128/78 |
| 4,622,957 | 11/1986 | Curlee . |
| 4,671,267 | 6/1987 | Stout ................................. 128/156 |
| 4,682,587 | 7/1987 | Curlee . |
| 4,682,588 | 7/1987 | Curlee . |
| 4,702,235 | 10/1987 | Hong ............................. 128/68.1 X |

Primary Examiner—Richard J. Apley
Assistant Examiner—J. Doyle
Attorney, Agent, or Firm—Poms, Smith, Lande & Rose

[57] ABSTRACT

The back support is constructed from a back brace of elastic material which carries a gel pad and an air bladder. The brace supports the pad against lower back of the user in firm engagement. The air bladder is juxtaposed and generally co-extensive with the pattern containing the gel-like material. The air bladder has three individually inflatable chambers, including left, right, and overall areas, so that the user may adjust the pressure exerted on the pad and hence the support of the lower back. The gel pad may also contain an adjustable heating element to electrically heat the gel-like material. The main portion of the back brace has two wide belt portions which extend forewardly and upwardly from the main lower back support area, and which are secured together by overlapping Velcro members at the lower stomach area; and the centerlines of these two wide belt portions may make an angle of about 30 degrees to 60 degrees with one-another. The air bladder assembly includes straps secured thereto which extend from the bladders per se through slits in the wide belts of the main portion of the back support and which straps are secured to the outer surfaces of the wide belts.

17 Claims, 7 Drawing Sheets

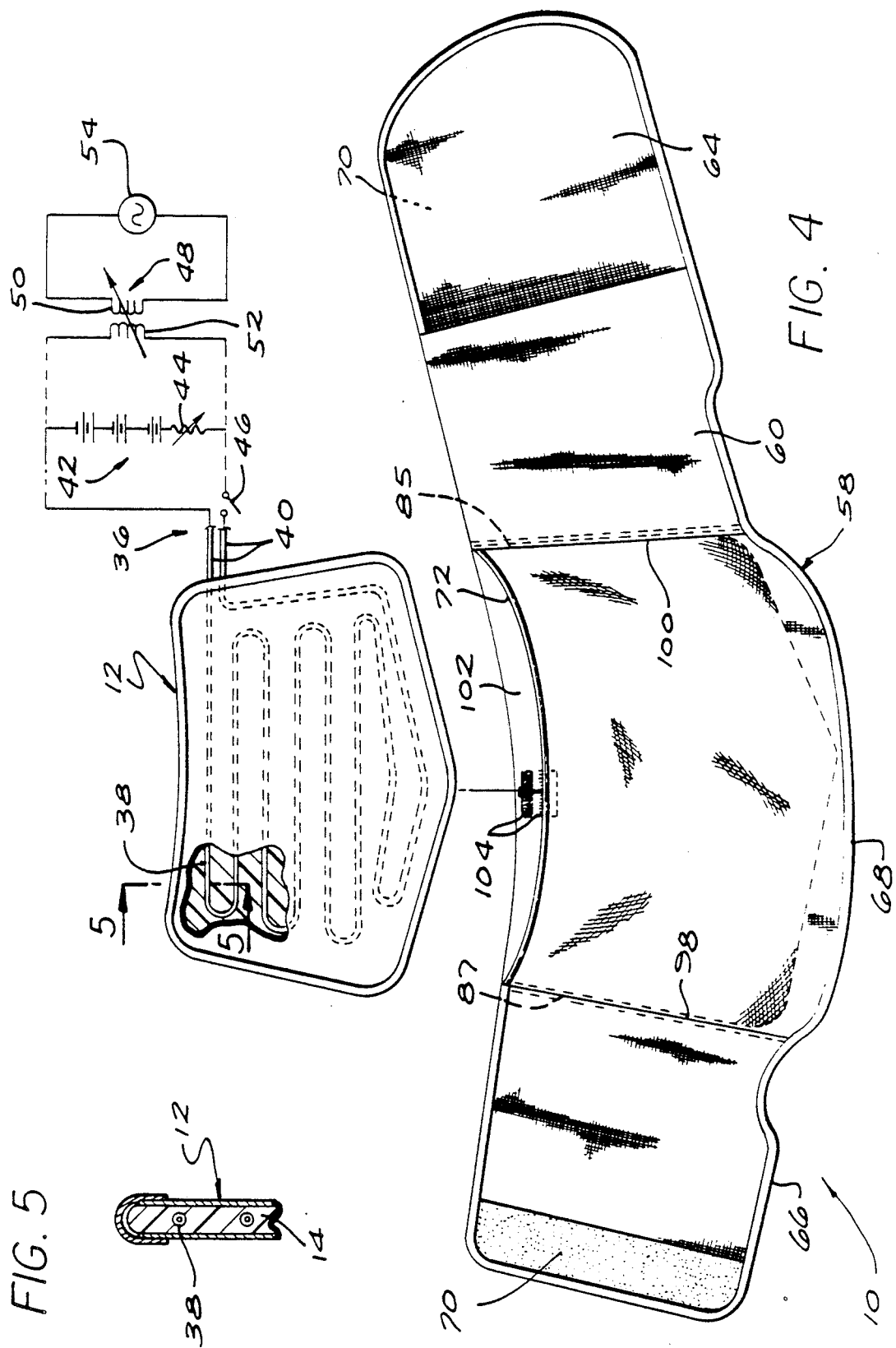

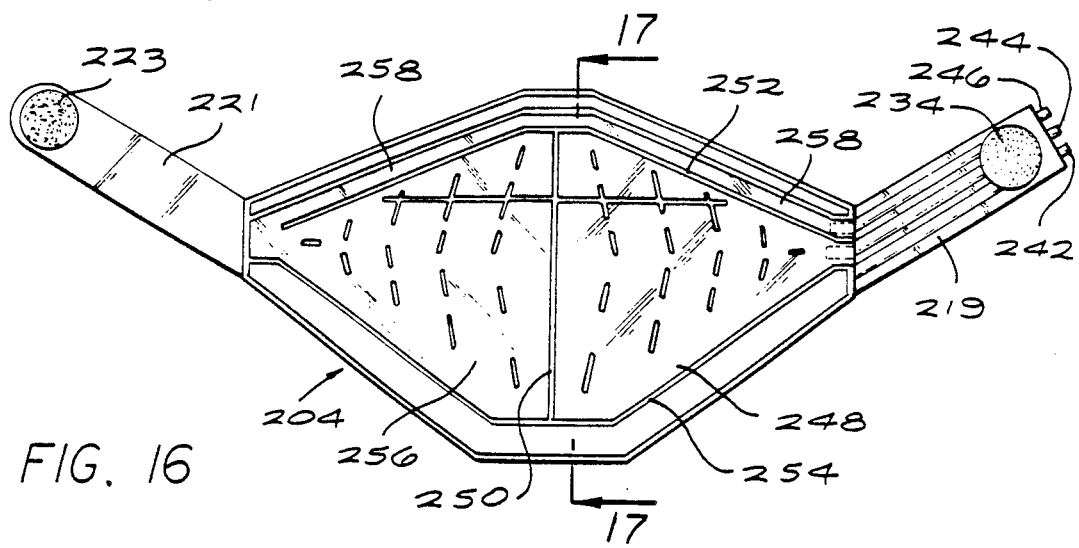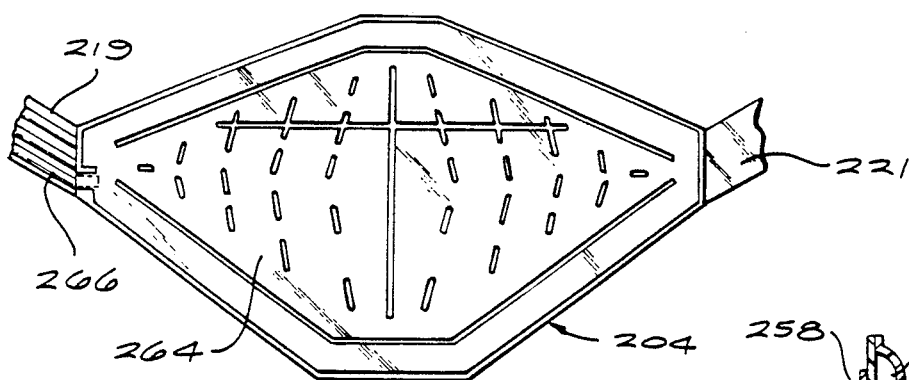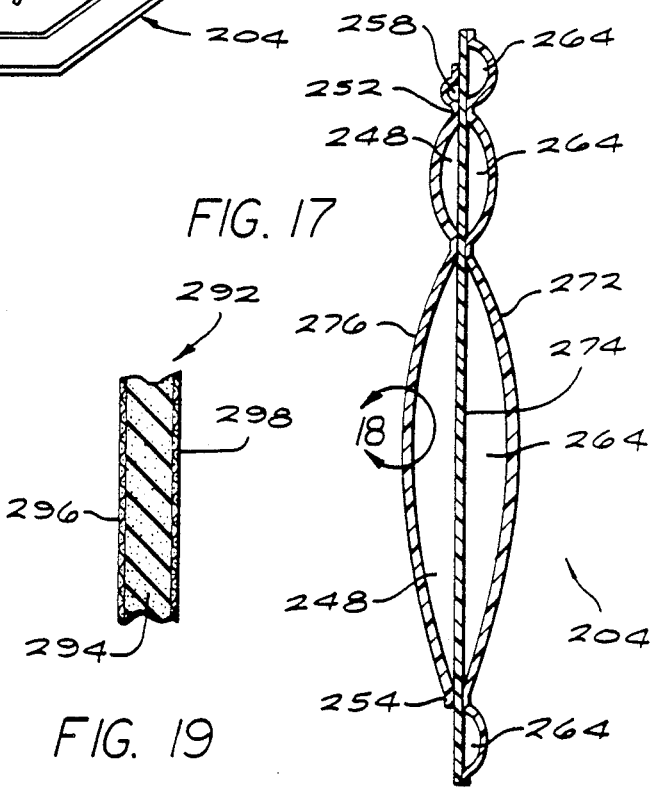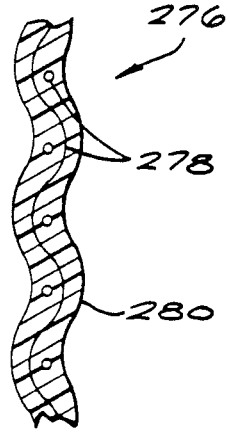

SIMPLIFIED ORTHOPAEDIC BACK SUPPORT

This application for letters patent is a Continuation-In-Part. co-pending application Ser. No. 07/308,687, filed Feb. 8, 1989 now U.S. Pat. No. 4,993,409.

Field of the Invention

The present invention relates generally to back supports, and more particularly, to a novel back support having a gel pad and an inflatable bladder to press the gel pad against the lower back of the user.

BACKGROUND OF THE INVENTION

Back supports having air inflatable bladders are known. For example, U.S. Pat. No. 4,622,957 (Curlee), discloses a therapeutic corset having an elongated support surface formed from material which is bendable when subjected to forces encountered thereby. A flexible cover is disposed on the support surface and secured thereto along its edges to form an envelope. The envelope has a plurality of cells, such that when the envelope is inflated, it assumes a predetermined curvature such as a crescent. When the corset is secured around a user, the envelope is held adjacent the sacrum lumbar and thoracic region of the body. Since the corset is formed from a relatively inelastic belting material, inflation of the envelope will exert a force against the above-mentioned body region. The envelope as described above has a plurality of vertical ribs which form the series of intercommunicating inflatable cells. The vertical ribs cause the envelope to shrink thereby insuring the tabular ribs always conform to the anatomy during a full range of movement. For example, see U.S. Pat. No. 4,682,587 (Curlee) which discloses one such envelope and U.S. Pat. No. 4,682,588 (Curlee) which discloses a vertical stack of interconnected envelopes.

A disadvantage and limitation of the above device is that the inflatable envelope is secured adjacent the body by relatively inelastic belting material. Such belting material if improperly secured about the torso may shift in position, negating the therapeutic effects of the corset, and also causing discomfort to the wearer.

In the treatment of spinal disorder, it is also desirable to use hot or cold therapy in conjunction with the support provided by a back brace. The devices described above in reference to the Curlee patents do not disclose such therapy.

It is accordingly an object of the present invention to overcome one or more of the limitations and disadvantages of the prior art above enumerated. It is another object of the present invention to provide a back brace adaptable for hot or cold therapy and adjustable by air inflation.

SUMMARY OF THE INVENTION

According to one aspect of the present invention, a back support includes a first pad having a gel-like substance contained therein and an air bladder co-extensive with, and juxtaposed to, the gel pad. The back support further includes means for supporting the gel pad in firm engagement against the lower back of a user and means for inflating the air bladder to press the pad against the lower back. The gel pad may further be removed for heating or cooling and reinserted prior to use for hot or cold therapy.

In one particular embodiment of the present invention, the air bladder has three chambers so that the user may adjust the pressure applied on the back according to the contours of the user's back. In preferred embodiments of the invention, two inner air bladders are provided, one on either side of the spine of the user, and a third, larger area, inflatable bladder is located behind the other two bladders to support and supply directed pressure to the gel pad and/or directly to the patient's back.

In another embodiment of the present invention, the back support further includes an electrical heating elements or wires disposed within the gel pad. External power either from a battery pack or from a wall outlet may supply current to the heating element. In the case of wall power current being used, a variable transformer allows the user to adjust the current in the heating element to adjust temperature.

In accordance with another aspect of the invention, it has been determined that it is preferable for the broad belt members, extending forwardly from a lower back pad, extend upwardly over the hips, and engage one another across the lower stomach area. The resultant geometry of the orthopaedic support includes the fact that the projected centerlines of the two broad belt members make an angle of about 30 degrees to sixty degrees with respect to one another. It is also noted that patients complaining of lower back problems often have protruding stomach areas. The engagement of the broad straps across the lower stomach area has the further advantageous factor of providing a corset-like upward pressure on this lower stomach area.

In accordance with a further feature of the invention, the inflatable bladder assembly has integrally associated straps which extend outwardly in alignment with, and exterior to, the main broad resilient belt members. In order for the inflatable bladders to be close to the patient, or to the thermal therapy pad, and for the straps for the inflatable bladder assembly to be on the outside of the main broad straps of the brace, these straps extend through slots through the main resilient brace construction on both sides of the main support area.

The brace may then be initially mounted on the patient and secured by large VELCRO pads or the like, and the inflatable bladder straps may then be pulled firm, and secured to the main broad brace belt members, also by VELCRO tabs or the like. The three inflatable bladders may then be inflated to apply the desired pressure to the lower back area.

VELCRO is a trademark, and the products sold under the VELCRO trademark are mating fabric pads, with one of the pads having its surface provided with a fine array of closely spaced outwardly protruding hooks, and the other of the mating pads being outwardly extending loops or other material with which the hooks may engage.

It is noted in passing that the multiple inflatable bladder assembly has a right-hand section, a left-hand section, and an overall section, which are separately inflatable. In some cases where lower back alignment correction is needed, this may be accomplished by providing more inflation to the left bladder and less to the right, or vice-versa.

In one embodiment, the features outlined above are implemented by a unit which has wide belts Q made of elasticized material, and pockets for selectively holding the thermal therapy pad and the inflatable bladder.

In a simplified embodiment, added in this Continuation-In-Part application, only three layers and three major parts are used: (1) the main support portion of the assembly, which is formed of two-way stretch material such as that found in a wet suit, with a central layer about ⅛ inch thick of foam rubber such as neoprene and two outer cloth, preferably nylon layers. Secondly, (2) the multiple bladder assembly is formed of cloth coated with plastic such as urethane to provide limited resiliency and an airtight construction, and is located on the main support by slits through the belt portions of the main support, which precisely match the width of the straps extending outwardly from the bladder assembly. The bladder assembly straps are firmly secured to the main support prior to inflation. The third and optional portion of the simplified assembly is (3) the thermal therapy pad which may be simply affixed to the inner surface of the bladder assembly by mating Velcro elements. To readily permit the use of the simplified construction without the thermal therapy pad, the stiffer type of VELCRO material (the hooks) are mounted on the thermal therapy pad, and the softer loop type material is mounted on the bladder assembly, so no discomfort is encountered by direct engagement of the back of the patient by the inner surface of the air bladder assembly.

These and other objects, advantages and features of the present invention will become apparent to those skilled in the art from a study of the following description of an exemplary preferred embodiment when read in conjunction with the attached drawings and appended claims.

BRIEF DESCRIPTION OF THE DRAWINGS

FIG. 4 is an exploded elevational view of the back support of FIGS. 1 and 2;

FIG. 5 is a cross-sectional view taken along line 5—5 of FIG. 4;

FIGS. 15 and 16 are inside and outside views, respectively, of the multiple inflatable bladder assembly, separate from the remainder of the assembly;

FIG. 17 is a cross-sectional vie:; taken along line 17—17 of FIG. 15;

FIG. 18 is a schematic showing of the construction of the bladder, as indicated at circle 18 in FIG. 17, indicating the inner woven material, coated with plastic material to provide an airtight seal for the surface; and FIG. 19 is a cross-sectional view; taken along line 19 of FIG. 14 to indicate the construction of the basic member of the embodiment of FIGS. 13–19.

DESCRIPTION OF THE PREFERRED EXEMPLARY EMBODIMENT

Figure 1:
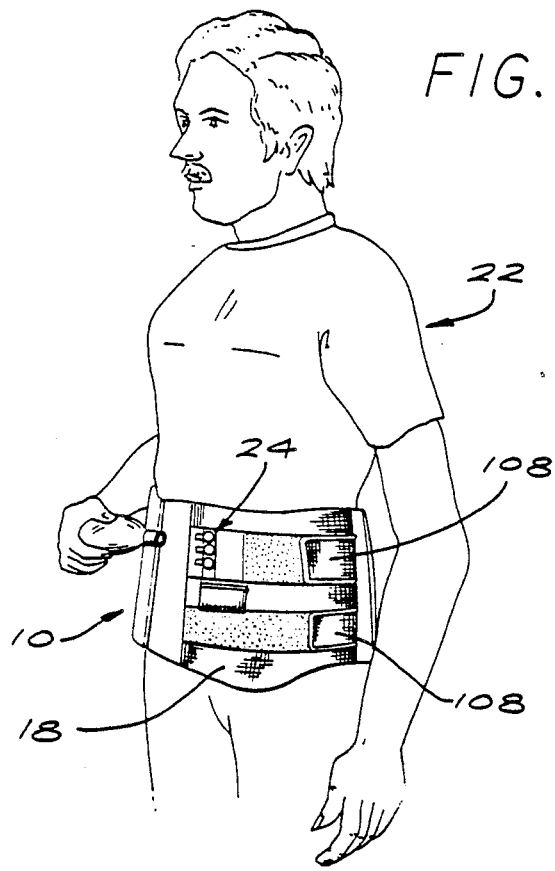
FIGS. 1 and 2 illustrate an intended use of a back support constructed according to the principles of the present invention.
Figure 2:
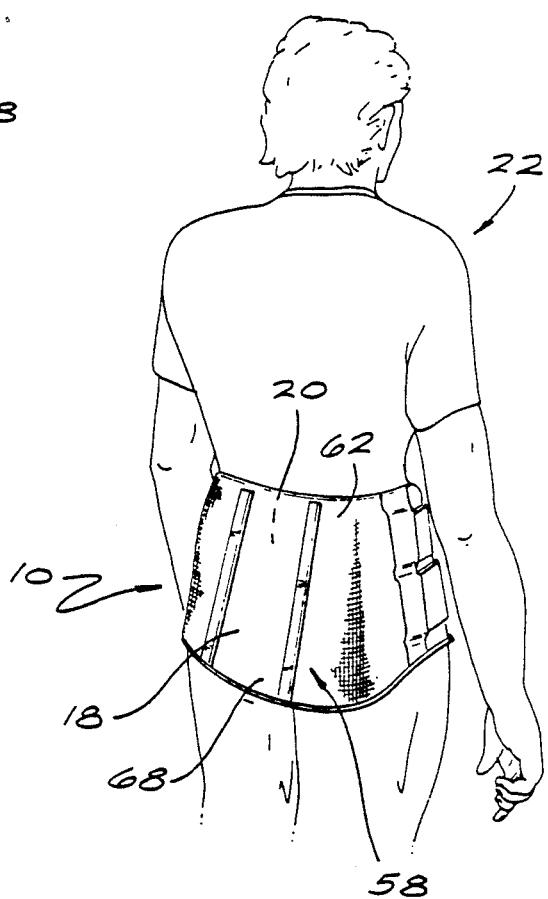
Figure 6:
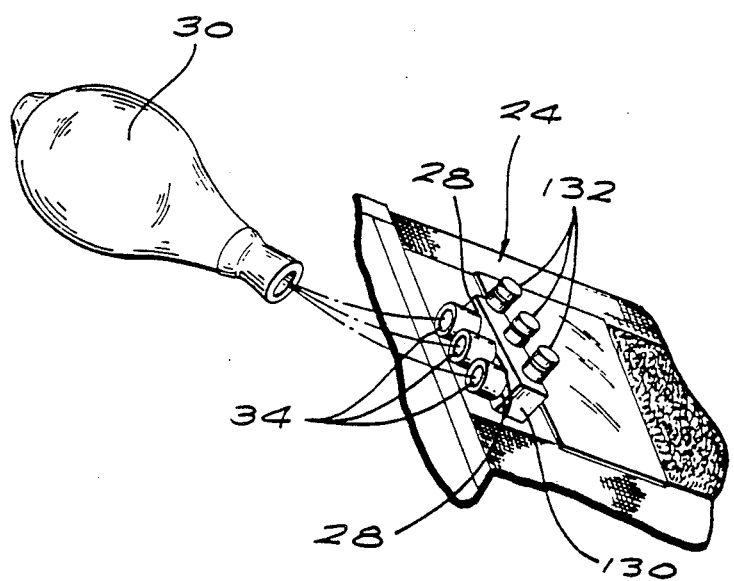
FIG. 6 is a enlarged perspective view of a portion of the back support involving inflation of the air bladders.
Figure 7:
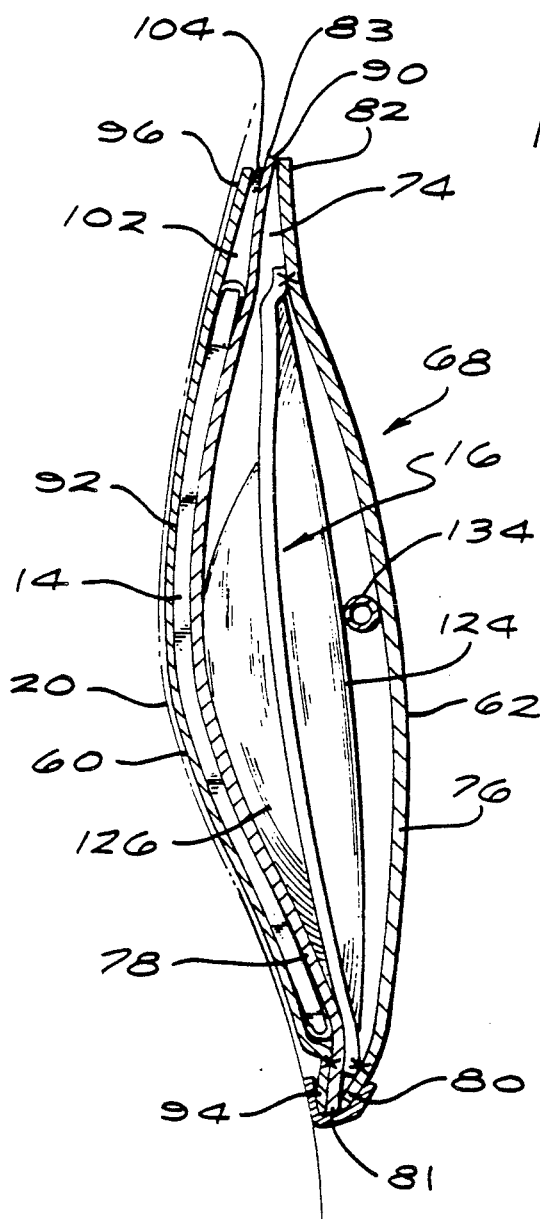
FIG. 7 is cross-sectional view taken along line 7—7 of FIG. 3.

Referring now to FIGS. 1–12, there is shown a back support 10 constructed according to the principles of the present invention. Back support 10 includes a thermal therapy pad 12 having a gel-like material 14 contained therein as best seen in FIG. 5 and FIG. 7, an air bladder 16, best seen in FIGS. 8–9, co-extensive with and juxtaposed to the thermal therapy pad 12, means 18 for supporting &:he pad 12 in firm engagement against the lower back 20 of a user 22, and means 24 for inflating the air bladder 16 to press the pad 12 against the lower back 20. The pad 12 of the gel-like material 14 is generally constructed from two sheets of vinyl which are sealed along their peripheral edges. The gel material 14 may be any conventional orthopaedic gel, such as Elasto Gel commercially available from Technologies Inc. of Kansas City, Mo. For a comfort to the user, the gel pad may be jacketed by a soft cloth (not shown).

Figure 8:
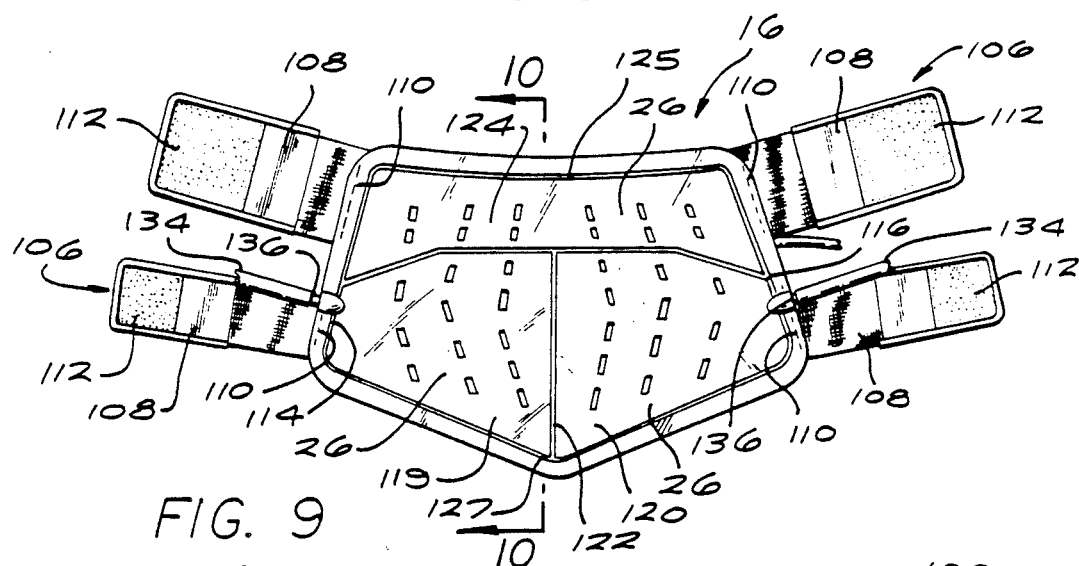
FIG. 8 is an elevational view of the air bladder used in the back support of FIGS. 1 and 2.
Figure 10:
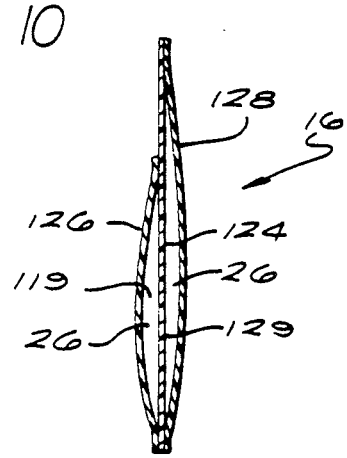
FIG. 10 is a cross-sectional view taken along line 10—10 of FIG. 8.
Figure 12:
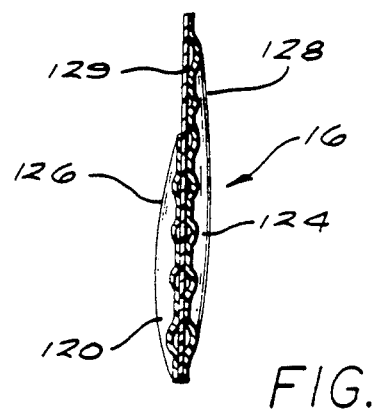
FIG. 12 is a cross-sectional view taken along line 12—12 of FIG. 9.

The air bladder 16 includes a plurality of chambers 26 as best seen in FIG. 8 and FIG. 10. Each of the chambers 26 are individually inflatable, as set forth in greater detail hereinbelow, by the inflating means 24.

Figure 3:
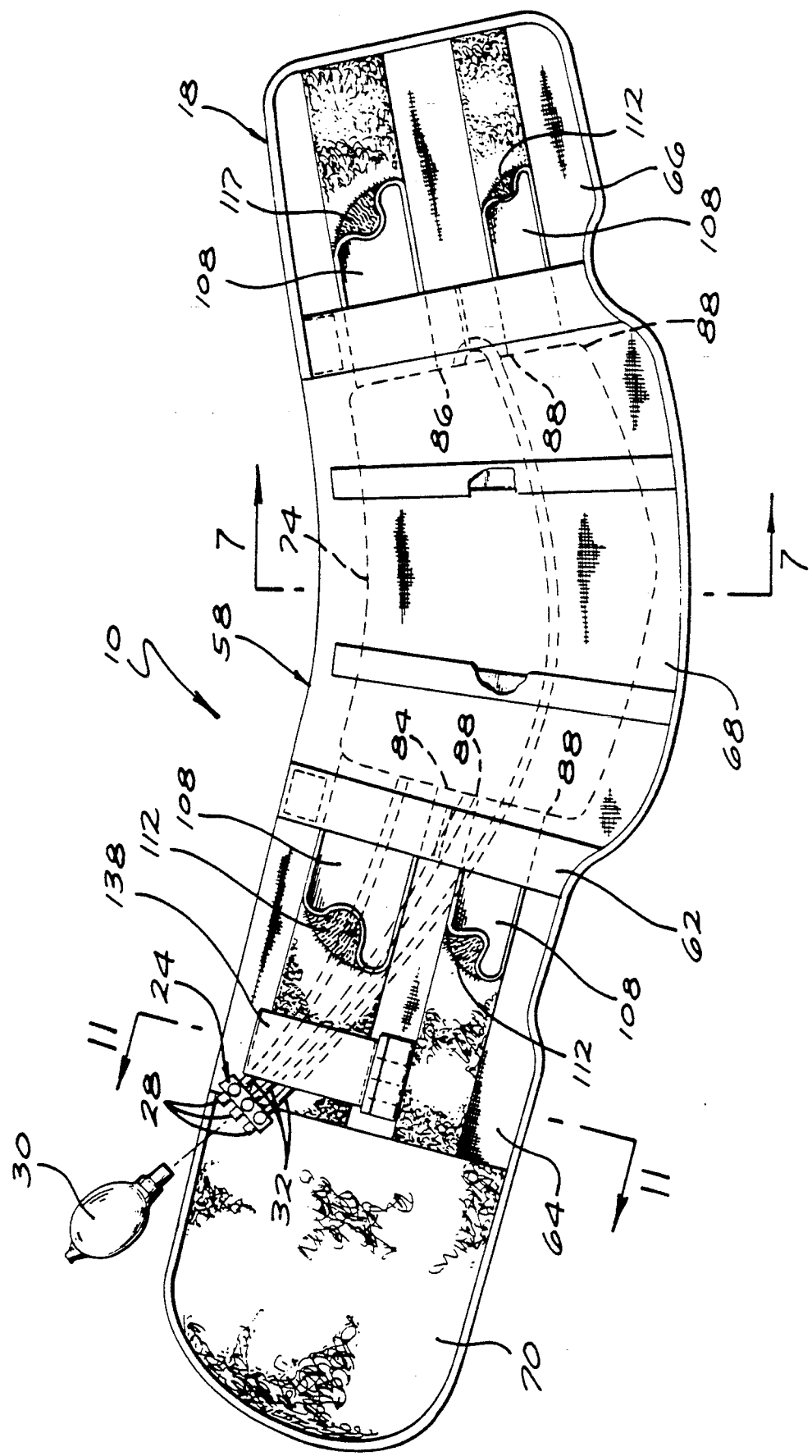
FIG. 3 is an elevational view, partially in phantom, of the back support shown in FIGS. 1 and 2.

Inflating means 24 includes a plurality of one-way valves 28 and an air pump 30 as best seen in FIG. 3 and FIG. 6. Each of the one-way valves 28 has an outlet 32 operatively communicating with the respective one of the chambers 26 of the air bladder 16 and an inlet 34. The air pump 30 is adapted for coupling to the inlet 34 of a user selected one of the one-way air valves 28. The air pump 30 may be a conventional squeeze ball.

Figure 11:
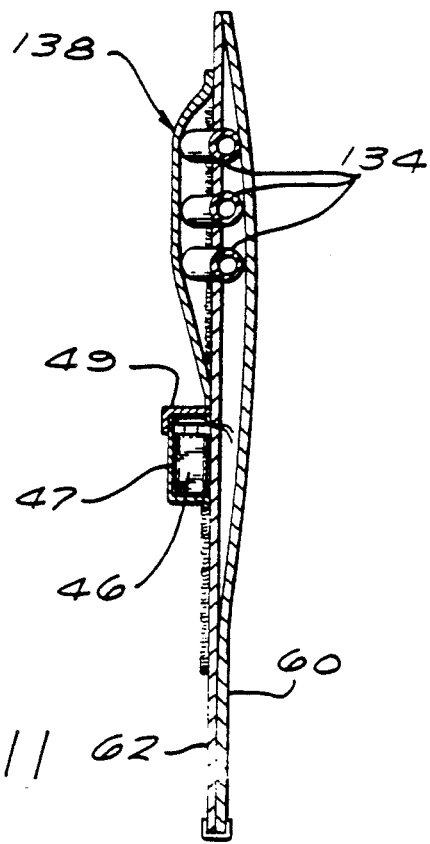
FIG. 11 is a cross-sectional view taken along line 11—11 of FIG. 3.

The back support 10, in a further embodiment of the present invention may also include means 36 for heating the gel-like material 14 as best seen in FIGS. 4–5. In an exemplary embodiment of the present invention, heating means 36 may include a resistive type electrical heating element 38 disposed within the pad 12 and surrounded by the gel-like material 14, and means 40 for conducting external electric power to the heating element 38. As best seen in FIG. 4, conducting means 40 may, in one embodiment of the present invention, include a source 42 of DC voltage electrically coupled to the heating element 38 through a rheostat 44 and a switch 46. The DC voltage source 42, rheostat 44, the switch 46 and the heating element 38 are all serially coupled in a single current loop. In an alternative exemplary embodiment of the present invention, conducting means 40 may include a variable transformer 48 having a primary 50 and a secondary 52. The primary coil 50 is adapted for coupling to a source of AC power 54, such as a conventional wall outlet. The secondary coil 52 is electrically coupled to the heating element 38 through the series coupled switch 46. The variable transformer 48 is adjustable by the user 22 to regulate the current through the heating element 38 to regulate the heating of the gel-like material 14, similarly to the rheostat 44 described hereinabove. Switch 46 may be a conventional push button type secured by a structural support 49. A flap of material 49 may totally enclose the switch 46 but still allow activation thereof, as best seen in FIG. 11.

The supporting means 18 is a brace 58 constructed of an elastic fabric and generally dimensioned to fit around the lower torso of the user 22 to support the pad 12 adjacent the lower back 20 as hereinabove described. The brace 58 includes an inner surface 60, an outer surface 62, a first section 64, a second section 66 and a third section 68 intermediate the first section 64 and the second section 66. The brace 58 further includes means 70 for releasably attaching the first section 64 to the second section 66 when the brace 58 is stretched around the torso thereby supporting the pad 12 in firm engagement against the lower back 22. For example, attaching means 70 may be a fastener available under the VELCRO trademark.

The third section 68 is dimensioned to be positioned adjacent the lower back 20 of the user 22 and has a first pocket 72 adjacent the inner surface 60 and a second pocket 74 intermediate the first pocket 72 and the outer surface 62. The pad 12 is removably received by the first pocket 72. The air bladder 16 is removably received by the second pocket 74.

As best seen in FIG. 7, the third section 68 of brace 58 includes a first sheet 66 and a second sheet of elastic fabric in a facing relationship and being of sufficient thickness and strength to provide support when stretched adjacent the lower back 20. Each of the first sheet 76 and the second sheet 78 respectively have a lower edge 80, 81 an upper edge 82, 83 and a pair of lateral edges 84, 85, 86, 87. The first sheet 76 and the second sheet 78 are joined
together at the respective lower edges 80, 81 and at selected points 88 along the lateral edges 84–87. The upper edge 82, 83 forms an opening 90 of the second pocket 74.

The third section 68 further includes a third sheet 92 of air permeable material such as a mesh type fabric in a facing relationship to the second sheet 78 and has a lower edge 94, an upper edge 96 and lateral edges 98, 100. The second sheet 78 and the third sheet 92 are joined together at the lower edge 81, 94 and at their respective lateral edges 85, 87, 98, 100. The upper edge 83, 96 of each of the second sheets 78 and third sheet 92 form an opening 102 of the first pocket 72. To keep the pad 12 within the first pocket 72, a VELCRO fastener 104 may be provided to keep the opening 102 closed.

Figure 9:
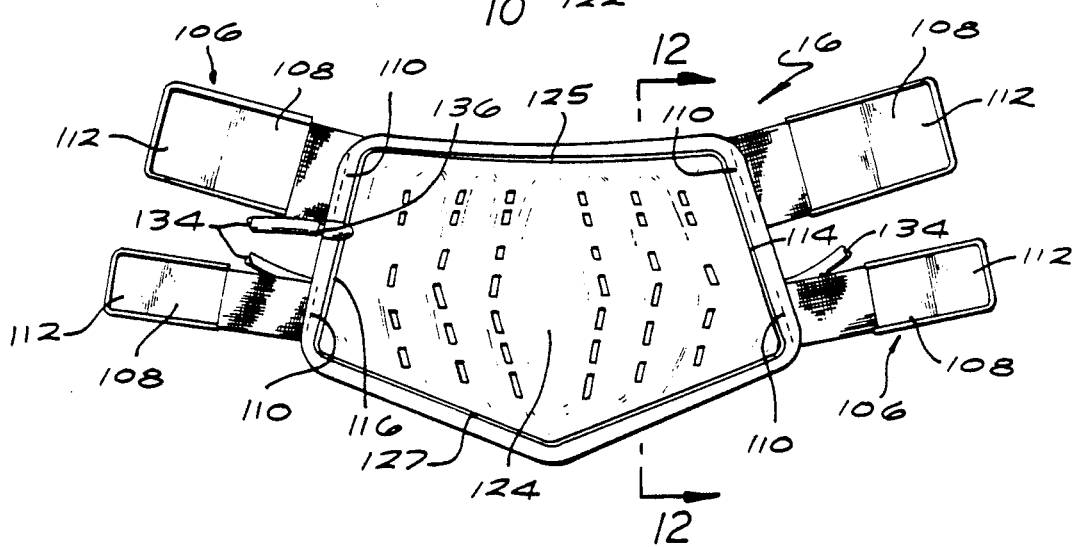
FIG. 9 is an elevational view of the opposite side of the air bladder shown in FIG. 8.

With particular reference to FIGS. 9–11, the air bladder 16 also includes means 106 for securing the bladder 16 within the second pocket 74. The securing means 106 includes a plurality of elongated straps 108 having a first end 110 and a second end 112. The first end 110 is affixed to the bladder 16. The straps 108 extend outwardly from the second pocket 74 between the selected points 88 along the lateral edges 84-87 of the first sheet 76 and second sheet 78. The second end 112 of t he straps 108 are releasably attached to an adjacent one of the first section 64 and the second section 66 of the brace 58. More particularly, the straps 108 are attached to the outer surface 62 of the brace 58. The straps 108 are constructed of elastic material, similar to the brace 10. After the brace 10 has been tightened about the user 22, the straps 108 provide for further adjustment of the pressure exerted on the lower back 20.

The bladder 16 further has a first lateral Q edge 114 and a second lateral edge 116. The first end 110 of a first pair of the straps 108 are affixed to the first lateral edge 114 and the first end 110 of a second pair of the straps 108 are affixed to the second lateral edge 116.

As described hereinabove, the bladder 16 includes a plurality of chambers 26. More particularly, the chambers 26 include a first chamber 119 and a second chamber 120. The first chamber extends substantially between the first lateral edge 114 and a vertical midpoint 122 bisecting the bladder 16. The second chamber 120 extends substantially between the second lateral edge 116 and the midpoint 122. Chambers 26 may further include a third chamber 124 extending between the first lateral edge 114 and the second lateral edge 116 of the bladder 26 and between an upper edge 125 and a lower edge 127 or the bladder 26.

In one embodiment of the present invention, bladder 26 may include a first wall 126, a second wall 128 and a third wall 129 in a facing relationship to each other. The first wall 126 is sealed to the third wall 129 at selected locations to form the first and second chambers 119, 120. The second wall 128 and the third wall 130 are sealed together to form the third chamber 124. In one embodiment of the present invention, the first wall 126, the second wall 128 and third wall 129 may be constructed from vinyl.

The first and second chambers 119, 120 occupy one side of the bladder 26 and the third chamber 124 is on the other side. The first and second chambers 119, 120 are also approximately two-thirds to three-fourths the height of the third chamber 124. The third chamber 124 has points 131 wherein the second wall 128 and the third wall 129 are sealed to each other to form intercommunicating cells 133. When inflated, the cells cause the bladder to assume an arcuate shape to conform to the lower back 20 and to exert a uniform force upon the gel pad 12, thereby pressing the gel pad 12 against the lower back 20. The first and second bladders 119, 120 are individually inflatable to adjust the pressure, somewhat laterally, against the lower back.

In one embodiment of the present invention, the inflating means 24 may include a valve assembly 130 which is carried by one of the first sections 64 and second section 66, as best seen in FIG. 6. The valve assembly includes the one-way valves 28 hereinabove described. Valve assembly further includes the plurality of pressure relief valves 132. Each of the pressure relief valves 132. Each of the pressure relief valves 132 is associated with an outlet 32 of a respective one of the one-way valves 28. The pressure relief valves are user activated to release pressure of respective one of the chambers 26. To operatively connect the outlet 32 to the respective one of the chambers 26, a tube 134 may be fitted over the outlet 32 and coupled to a fitting 136 mounted through either the first walls 126 or second wall 128 of the bladder 26 to communicate with the respective one of the first chamber 118, second chamber 120 or third chamber 124. A support structure 138 may be attached to the outer surface 62 of the first 64 to carry the valve assembly 130 and parts of tubes 134.

Figure 13:
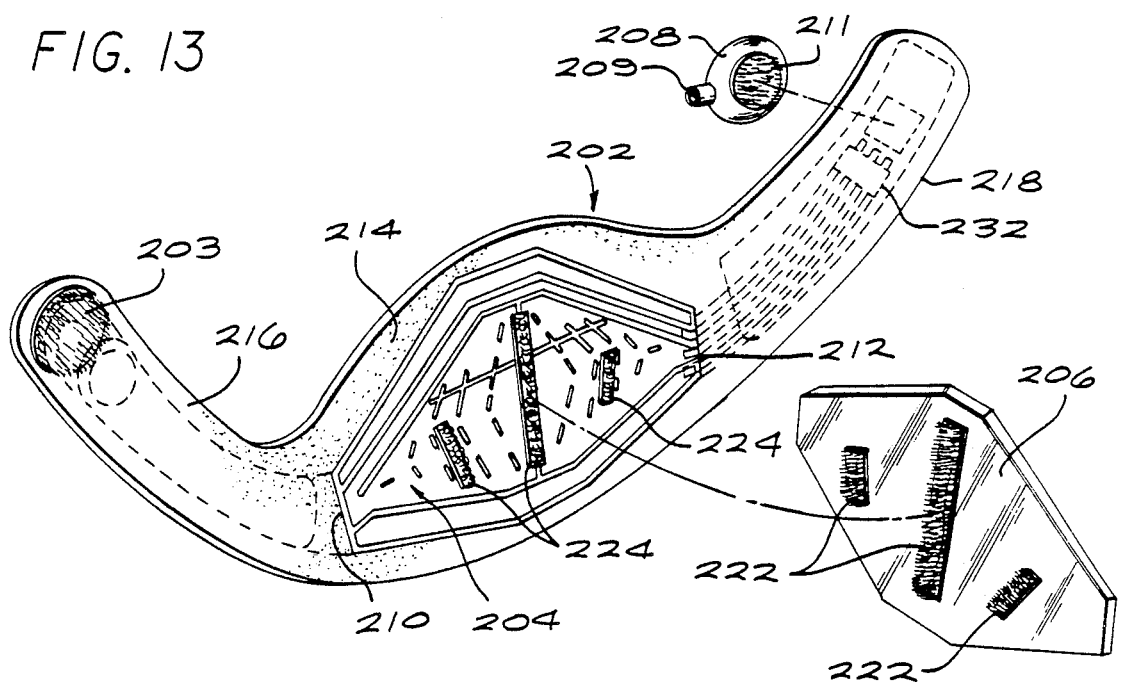
FIG. 13 is an exploded view of another simplified embodiment of a back support using both thermal therapy devices and multiple inflatable bladders.

FIGS. 13 through 19 relate to a simplified form of back brace or support. FIG. 13 is an exploded view taken from the inside of the back support, and showing the main support member 202 of the assembly, the air bladder assembly 204, and the thermal therapy pad 206. Also shown in FIGS. 13 and 14 separate from the main assembly, is a small flexible hand pump 208 which may be kept assembled with the back support or separate therefrom, and which may be used to selectively control the air applied to each of the three air bladders. The big circular VELCRO pac 203 makes engagement with VELCRO strip 225 to hold the support assembly symmetrically around the body of the patient.

Figure 14:
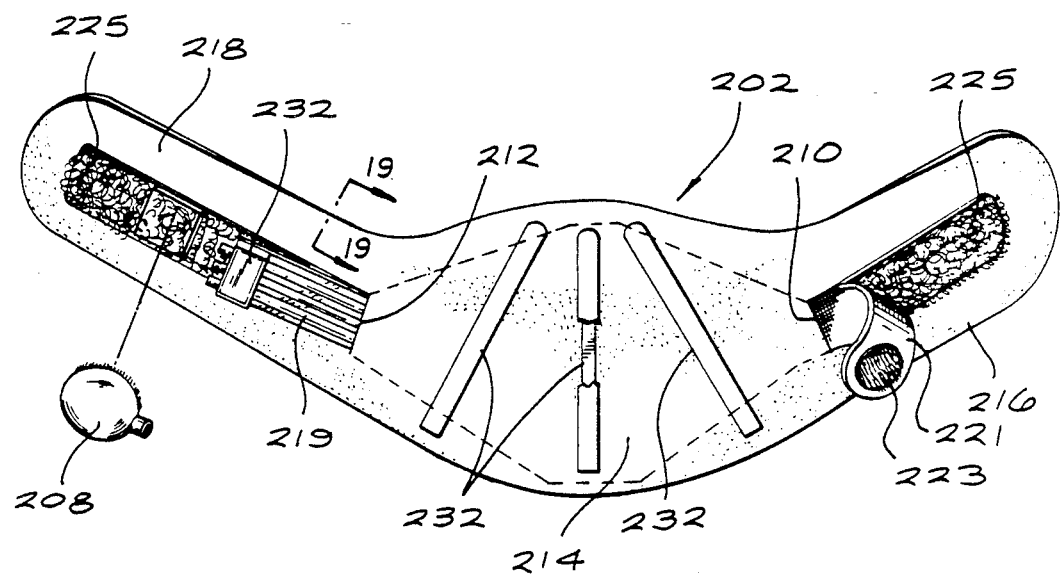
FIG. 14 shows the outside of the back support of FIG. 13.

FIG. 14 is a perspective view of the outside of the support, the other side from that shown in FIG. 13. Particularly to be noted in FIGS. 13 and 14 are the slits 210 and 212 at each side of the wide main portion 214 of the main support member 212 where it merges into the two wide belt-like members 216 and 218 which extend upwardly and outwardly from the area 214. After the arms 219 and 221 forming part of the air bladder assembly 204 are pulled through the slits 212 and 210, respectively, they are tensioned and secured by VELCRO pads 223 to VELCRO strips 225 extending along belt members 216 and 218.

Also shown in FIG. 13 are VELCRO strips 222, the thermal therapy or gel pad 206, and the mating VELCRO pads 224 on the inner surface of the air bladder assembly 204. As is well known, VELCRO is a trademarked product and is made up of a mating pair of fabrics, one of which includes a series of relatively stiff hooks and the other includes loops, and can be implemented by many known fabrics which are relatively soft in nature. In the present case, where the back support may be employed without the thermal therapy pad 206, it is preferably the pads 222 which are the stiffer hooks be mounted on the gel or thermal therapy pad 206, with the pads 224 on the bladder assembly being of the softer loop material, so as not to be uncomfortable upon direct engagement with the patient.

To avoid undue bending or buckling or the back support, three thin flexible stays 232 are provided, mounted either permanently or removable in sewn-in sleeves on the outer surface of member 202.

The air bladder assembly 204 may be formed integrally with the straps 219 and 221 to provide an assembly which is of high strength, and also has the desirable attributes of inflatability and considerable resilience. One material which meets these needs is a nylon fabric, lightly but continuously coated with urethane at about 3 or 4 ounces of urethane per square yard of fabric material. However, greater or lesser amounts of various plastics may be used and any of a number of open or closed weave fabrics may be employed.

Proceeding to a consideration of additional figures of the drawings, FIGS. 15 through 18 all relate to the air bladder assembly, with the VELCRO material 224 shown in FIG. 13 having been removed from the showings of FIGS. 15-18 for clarity of depiction of the remaining structure.

In this regard, FIG. 15 shows the inner surface of the air bladder assembly 204 with the integral securing strap member 219 which also includes the air channels and valve assembly 232, (covered by a VELCRO pad in FIG. 15), and the second strap member 221 with its large VELCRO pad 223 for securing to mating VELCRO strip 225, as shown to the right in FIG. 14. Strap 219 has a similar circular VELCRO pad at reference numeral 234 in FIG. 15, for securing to the mating broad VELCRO strip 225 on the other arm 218 of the basic support 202.

The air bladder assembly has three separately inflatable bladders, which may be inflated by pumping air by the pump 208 to a selected one of the three inputs 242, 244, and 246. On the inner surface of the bladder assembly, as shown in FIG. 15, there is a left-hand bladder 348 bounded by the central plastic bonding line 250 and the upper and lower plastic heat-sealed bonding lines 252 and 254, and being coupled at its right-hand end to an air channel in strap 219, leading in turn to the central check inlet valve 244. A similar right-hand, inner inflatable bladder 256 is inflated from inlet 246 via channel 258 extending to the left-hand end of bladder 256.

FIG. 16 shows the other side of the assembly, and the overall bladder 264 which extends for virtually the entire area of the main portion of bladder assembly 204, and is inflatable via the lowermost channel 266 included in strap 219.

FIG. 17 is a cross-sectional view taken along line 17 of FIG. 15, and cuts through the left-hand bladder 248, the overall, back-up bladder 264, and the channel 258 for inflating the right-hand bladder 256. From FIG. 17, it may be seen that the bladder assembly is formed of three layers 272, 274 and 276 of airtight material of fairly high strength, heat-sealed together as shown in FIGS. 15, 16, and 17.

FIG. 18 is a diagrammatic showing of an enlarged cross-section of the sheet material, such as sheet 276, used in the formation of the air bladder assembly. As mentioned above, there is a core of open or closed weave material, and it has a thin coating 280 of plastic material, such as urethane applied to it to make it airtight. With the plastic layer being so thin, the outer surface of the composite sheet material follows the contours of the underlying cloth, but is now airtight and of significantly increased mechanical strength. The total thickness of the material is only one - one hundredth of an inch thick or less.

FIG. 19 represents the cross-section of a much thicker composite material, that of the main base or support member 202 of FIGS. 13 and 14, and FIG. 19 is taken along line 19 of FIG. 14. The composite layer 292, as shown in FIG. 19 is about one-eighth inch thick, and includes a central core of foam rubber 294 to which are bonded layers 296 and 298 of finely woven cloth, such as nylon. The resultant composite material is known and is used for making "wet suits" for winter surfboarding activities, or the like. The material is flexible and resilient, and it will stretch about 20 percent with moderate forces of 5 to 20 pounds per inch.

For completeness, other dimensions and angles of interest relating to the illustrative embodiments, will be given. In this regard, it is again noted that the main area for the application of thermal therapy and pressure is the lower back, and the two main belt-like members extend upwardly and forwardly around the waist joining at the lower stomach area. It is interesting to note that, when the back supports are lying flat on a surface, and when the centerlines of the belt members are extended, the outwardly directed angles between these centerlines is about 30 degrees for one embodiment, and about 45 to 55 degrees for the other embodiment. More specifically, with reference to FIG. 14, if the centerlines of the two arms of the belt member are extended so that the centerlines cross each other, there are two equal outwardly directed angles, and equal upwardly and downwardly directed angled. One specific set of dimensions for a medium size back support as shown in FIGS. 13-19 will now be given. First, the overall size of the symmetrical unit is about 36 inches, the width of each of the belts is about 5-½ or 6 inches, and the size of the main back support area is about 10×15 inches.

Concerning another aspect of the embodiments, it may be noted that the pump 30 and the inlet 28 valving arrangements 24, as shown in FIG. 3, may be implemented by the flat pump 208 and inlet valve assembly 232, as shown in FIGS. 13 and 14. The flat pump 208 may be formed of two circular airtight members of the type of material described in FIG. 18, sealed around their edges, mechanically biased to the expanded state, and coupled to a standard size plastic tube 209. The flat pump 208 may be provided with a VELCRO pad 211 for securing it to the assembly. The inlet and valve assembly 232 may include check valves and relief valves for each of the multiple bladders. If desired, the pump 208 may be permanently coupled to the inlet and valve assembly 232 may be provided with internal control for directing air to the desired bladder. or alternatively, the pump may be manually shifted to the desired inlet channel.

There has been described above an exemplary preferred embodiment of a novel back brace. It should be apparent that those skilled in the art may now make numerous usage of and departures from the above-described exemplary embodiment without departing from the inventive concepts described herein. Thus, by way of example but not of limitation, instead of the fully elasticized materials as disclosed hereinabove, the main body of the back support may be formed of a flexible material with relatively little of no substantial stretch; in fact, the angled configuration of the brace permits practical use of this type of back support using such materials. Accordingly, the present invention is to be defined solely by the scope of the following claims.

What is claimed is:

1. A simplified inflatable back support assembly comprising:
   a main body member formed of elasticized material for extending continuously at least around both sides and the back of a patient;
   said body member having an enlarged central area formed of said elasticized material for covering the lower back;
   said body member having first and second arm means formed of said material for holding said back support assembly around the mid-section of the patient;
   an inflatable assembly including a central inflatable bladder substantially co-extensive in configuration with said enlarged central area of elasticized material;
   said inflatable assembly including at least two straps or thin arms directly secured to said bladder and extending outwardly along said first and second arm means and being substantially thinner than said arm means;
   said first and second arm means being provided with transverse slits adjacent said central area to permit the passage of said straps therethrough, with the bladder on the inside of the enlarged central area of the main body member and said straps starting inside said main body member where said straps are secured to said bladder, and then extending along the outside of said main body member after passing through said slits;
   means for adjustably securing the outer ends of said first and second arm means together to provide an initial coarse fit of said back support assembly onto said patient;
   means for adjustably securing said straps to the outer surfaces of said arm means to provide a vernier fit of said back support assembly onto said patient; and
   means for selectively applying air to said bladder assembly to provide a final therapeutic and comfort fit to said back support assembly.

2. A back support assembly as set forth in claim 1 wherein said air bladder has a plurality of chambers, including at least one left-hand chamber and one right-hand chamber, each of said chambers being individually inflatable by said inflating means.

3. A back support assembly as defined in claim 1 further comprising a thermal therapy pad, and means for mounting it on said assembly for applying thermal therapy to the user's back.

4. A back support as set forth in claim 3 further comprising:
   means for heating said thermal therapy pad.

5. A back support assembly as defined in claim 1 wherein said arm means extend upwardly and outwardly from said enlarged central area, and wherein the extended centerlines of said arm means make an outwardly directed angle of between 30 degrees and sixty degrees with respect to one-another.

6. A back support assembly as defined in claim 1 wherein substantially the only arrangements for holding said assembly together are said slots with the straps extending through the slits, and additional securing material, including mating pads or hook type material and loop type material.

7. A back support assembly comprising:
   a main body member having a central enlarged area for covering most of the lower back;
   a composite air bladder mounted co-extensive with and juxtaposed to said central area of said main body member;
   said composite air bladder including a left-hand, separately inflatable bladder means for applying pressure to the left-hand side of the lower back;
   said composite air bladder further including a right-hand separately inflatable bladder means for applying pressure to the right-hand side of the lower back;
   means for inflating said left-hand or said right-hand bladder means to a greater extent than the other bladder means to apply differential pressure to the two sides of the lower back; and
   a main inflatable bladder means forming part of said composite inflatable bladder, and being located behind and extending over both the left and right-hand bladder means, thereby constituting means for applying increased pressure to both said left and right-hand bladder inn their application of pressure to the patient's back.

8. A back support assembly as defined in claim 7 further comprising a thermal therapy pad, and means for mounting it on said assembly for applying thermal therapy to the user's s back.

9. The back support as set forth in claim 8 further comprising:
   means for heating said thermal therapy pad.

10. A simplified inflatable back support assembly comprising:
    a main body member formed of two-way stretch material for extending continuously at least around both sides and the back of a patient;
    said body member having an enlarged central area formed of said material for covering the lower back;
    said body member having first and second arm means formed of said material for holding said back support assembly around the mid-section of a patient;
    an inflatable assembly including a central bladder substantially co-extensive in configuration with said enlarged central area formed of two-way stretch material;

said inflatable assembly including at least two straps or thin arms extending outwardly along said first and second arm means and being substantially thinner than said arm means;

said first and second arms being provided with transverse slits adjacent said central area to permit the passage of said straps therethrough, with the bladder on the inside of the enlarged central area of the main body member and said straps starting inside said main body member where said straps are secured to said bladder, and then extending along the outside of said main body member after passing through said slits;

means for adjustably securing the outer ends of said first and second arms together to provide an initial coarse fit of said back support assembly onto said patient;

means for adjustably securing said straps to the outer surfaces of said arms to provide a vernier fit of said back support assembly onto said patient;

means for selectively applying air to said bladder assembly to provide a final therapeutic and comfort fit to said back support assembly; and a thermal therapy pad mounted to the front of said inflatable assembly, to provide thermal therapy to the lower back of a user.

11. A back support assembly as defined in claim 10 wherein said arm means extend upwardly and outwardly from said enlarged central area, and wherein the extended centerlines of said arm means make an outwardly directed angle of 30 degrees and sixty degrees with respect to one-another.

12. A back support assembly as defined in claim 10 wherein substantially the only arrangements for holding said assembly together are said slits with the straps extending through the slits, additional securing material, including mating pads of hook type material and loop type material.

13. A back support assembly as defined in claim 10 wherein said inflatable assembly includes separately inflatable left-hand and right-hand bladders.

14. A back support assembly as defined in claim 13 wherein said inflatable assembly further includes an overall separately inflatable bladder extending over said left and right-hand bladder.

15. A simplified inflatable back support assembly comprising:
a main body member formed of flexible elastic material for extending continuously at least around both sides and the back of a patient;
said body member having an enlarged central area formed of said flexible elastic material for covering the lower back;
said body member having first and second arm means formed of said material for holding said back support assembly around the mid-section of the patient;
an inflatable assembly including a central bladder substantially co-extensive in configuration with said enlarged central area;
said inflatable assembly including at least two straps or thin arms secured to said bladder and extending outwardly along said first and second arm means and being substantially thinner than said arm means;
said first and second arm means being provided with transverse slits adjacent said central area too permit the passage of said straps therethrough; with the bladder on the inside of the enlarged central area of the main body member and said straps starting inside said main body member where said straps are secured to said bladder, and then extending along the outside of said main body member after passing through said slits;
means for adjustably securing the outer ends of said first and second arm means together to provide an initial coarse fit of said back support assembly onto said patient; and
means for adjustably securing said straps to the outer surfaces of said arm means to provide a vernier fit of said back support assembly onto said patient; and
means for selectively applying air to said bladder assembly to provide a final therapeutic and comfort fit to said back support assembly.

16. A simplified back support assembly comprising:
a main body member formed of flexible and resilient material for extending continuously at least around both sides and the back of a patient;
said body member having an enlarged central area formed of said flexible resilient material for covering the lower back;
said body member having first and second arm means formed of said material for holding said back support assembly around the mid-section of the patient;
a pressure application assembly including means for applying resilient pressure to the back of the patient substantially co-extensive in configuration with said enlarged central area;
said pressure application assembly including at least two straps or thin arms secured to said pressure applying means and extending outwardly along said first and second arm means and being substantially thinner than said arm means;
said first and second arm means being provided with transverse slits adjacent said central area to permit the passage of said straps therethrough, with the pressure applying means on the inside of the enlarged central area of the main body member and said straps starting inside said main body member where said straps are secured to said bladder, and then extending along the outside of said main body member after passing through said slits;
means for adjustably securing the outer ends of said first and second arm means together to provide an initial coarse fit of said back support assembly onto said patient; and
means for adjustably securing said straps to the outer surfaces of said arms to provide a vernier fit of said back support assembly onto said patient.

17. A simplified inflatable back support assembly comprising:
a main body member formed of elasticized material for extending continuously at least around both sides and the back of a patient;
said body member having an enlarged central area formed of said elasticized material for covering the lower back;
said body member having first and second arm means formed
said body member having first and second arm means formed of said material for holding said back support assembly around the mid-section of the patient;
a bladder assembly including a central bladder substantially co-extensive in configuration with said enlarged central area of elasticized material, said bladder including means for confining gas therein;

said bladder assembly including at least two straps or thin arms directly secured to said bladder and extending outwardly along said first and second arm means and being substantially thinner than arm means;

said first and second arm means being provided with transverse slits adjacent said central area to permit the passage of said straps therethrough, with the bladder on the inside of the enlarged central area of the main body member and said straps starting inside said main body member where said straps are secured to said bladder, and then extending along the outside of said main body member after passing through said slits;

means for adjustably securing the outer ends of said first and second arm means together too provide an initial coarse fit of said back support assembly onto said patient;

means for adjustably securing said straps to the outer surfaces of said arm means to provide a vernier fit of said back support assembly onto said patient; and said bladder assembly providing a supplemental therapeutic and comfort fit to said back support assembly.

* * * * *